United States Patent [19]
Williamson et al.

[11] Patent Number: 5,811,095
[45] Date of Patent: Sep. 22, 1998

[54] BASAL AND CHITINASE BROTH COMPOSITIONS FOR ENHANCING ANTI-FUNGAL ACTIVITY OF A CHEMICAL FUNGICIDE AND METHODS FOR PREPARING AND USING SAME

[75] Inventors: John B. Williamson, Visalia; David Schulteis, Fresno, both of Calif.

[73] Assignee: Alternative Methods, Inc., Visalia, Calif.

[21] Appl. No.: 602,205

[22] Filed: Feb. 20, 1996

Related U.S. Application Data

[63] Continuation-in-part of Ser. No. 439,432, May 11, 1995, which is a continuation-in-part of Ser. No. 54,228, Apr. 30, 1993, abandoned.

[51] Int. Cl.$^6$ .......................... A61K 38/54; A01N 25/00; C12N 9/00
[52] U.S. Cl. .................. 424/94.2; 424/405; 424/94.21; 424/94.61; 424/94.65; 435/186; 435/209; 435/219
[58] Field of Search .............................. 424/94.65, 94.2, 424/94.1, 94.63, 94.21, 600, 601, 602, 405; 536/56; 435/209, 186, 219, 224

[56] References Cited

U.S. PATENT DOCUMENTS

| | | | |
|---|---|---|---|
| 3,862,007 | 1/1975 | Smirnoff | 435/206 |
| 3,911,110 | 10/1975 | Smirnoff | 424/93.461 |
| 4,686,185 | 8/1987 | Wakunaga et al. | 435/206 |
| 4,751,081 | 6/1988 | Suslow et al. | 424/93.2 |
| 4,759,933 | 7/1988 | Uchida et al. | 426/7 |
| 4,855,133 | 8/1989 | Kamei et al. | 424/84 |
| 4,940,840 | 7/1990 | Suslow et al. | 800/205 |
| 5,118,503 | 6/1992 | Sawai et al. | 424/195.1 |
| 5,173,419 | 12/1992 | Harman et al. | 435/209 |

FOREIGN PATENT DOCUMENTS

| | | |
|---|---|---|
| 1228756 | 11/1966 | Germany . |
| 49125520 | 12/1974 | Japan . |

OTHER PUBLICATIONS

Cano and Colome, "Microbiology", (West Publishing Co.: New York) (1986) pp. 567, 721.

"Farm Chemical Handbook '95", (1995) pp. F50–F73 (Meister Publishing: Willoughby, OH).

Lorito et al. "Synergistic interaction between fungal cell wall degrading enzymes and different antifungal compounds enhances inhibition of spore germination", Microbiology (1994) 140: 623–29.

Watanabe et al. "Effects of fungal enzymes and non–ionic detergents on the actions of some fungicides against Pyricularia oryzae", Agric. Biol. Chem. (1988) 52: 895–901.

Beaulatonn "Cytochemical electron–microscopic study of the cuticular initima of the insect trachea. Action of chitinase and proteases on ultrafine tissue sections", C.R. Acad. Sci., Ser. D (1969) 269(24): 2388–91 (abstract only), 1969.

*Primary Examiner*—Jean C. Witz
*Assistant Examiner*—Susan Hanley
*Attorney, Agent, or Firm*—Daniel J. Meaney, Jr.

[57] ABSTRACT

An insecticidal composition and its method of preparation are presented. The composition comprises a basal broth, a chitinase broth and a chemical fungicide. The basal broth has proteins hydrolyzed by papain and pancreatin while the chitinase broth is prepared by fermenting chitin and a chitinase-producing bacterial culture. The insecticidal composition has synergistic activity.

32 Claims, 5 Drawing Sheets

N-ACETYL-GLUCOSAMINE

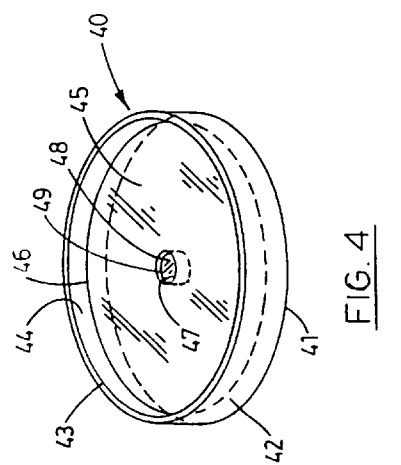
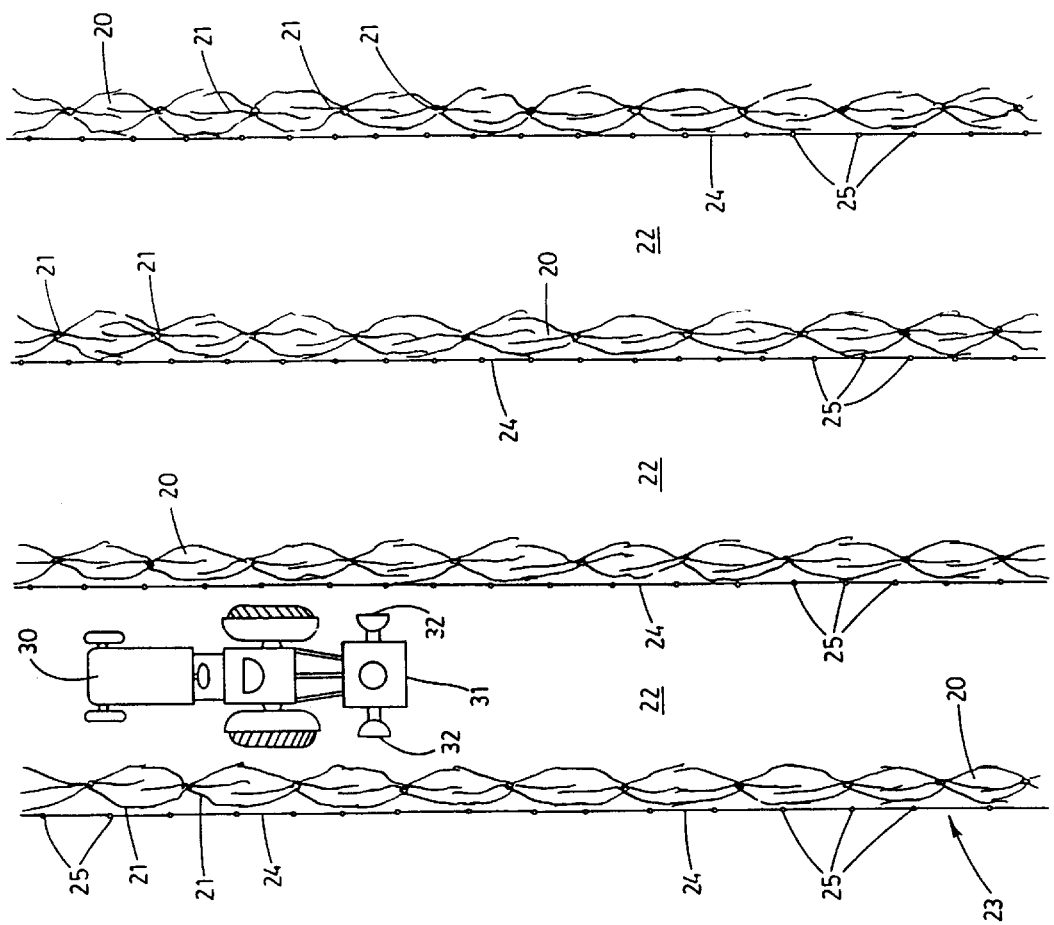

| TEST | MIXTURE | KILLING EFFECT ON FUNGUS AND NEMATODES |
|---|---|---|
| 1* | CB | LOW |
| 2* | BB | HIGH |
| 3* | CB/BB RATIO 1:1 | HIGH |
| 4** | CB/BB RATIO 1:2 | MEDIUM |
| 5** | CB/BB RATIO 2:1 | LOW-MEDIUM |

CB = CHITINASE BROTH
BB = BASAL BROTH
\* = ACTUAL RESULTS
\*\* = EXTRAPOLATED RESULTS BASED ON ACTUAL RESULTS

Fig 7

BASAL AND CHITINASE BROTH COMPOSITIONS FOR ENHANCING ANTI-FUNGAL ACTIVITY OF A CHEMICAL FUNGICIDE AND METHODS FOR PREPARING AND USING SAME

RELATED APPLICATIONS

This Application is a Continuation-in-Part of U.S. Pat. application Ser. No. 08/439,432 filed May 11, 1995, a pending application, which in turn was a Continuation-in-Part of U.S. Pat. application Ser. No. 08/054,228 filed Apr. 30, 1993, now abandoned.

BACKGROUND OF THE INVENTION

1. Field of the Invention

The present invention relates to a basal broth and chitinase broth composition having a synergistic chemical fungicide and method for preparing and using the same, and, more particularly to compositions comprising a chemical fungicide and basal broth and chitinase broth composition or solution of basal broth alone and methods for preparing and using the same. The combination of the chemical fungicide and basal broth in combination with the chitinase broth or the chemical fungicide and the basal broth alone are particularly well suited to use in the control of certain pests, insects or fungi without undue hazard to humans, animals or the environment.

In addition, the chitinase broth can be used alone as an inhibitor chemical agent for chitin-containing fungi, pests, or insects, such as nematodes, and to enhance plant growth by biological control of plant pathogens.

The chitinase broth may have a fermented solution of dipotassium phosphate, magnesium sulfate, iron (II) sulfate heptahydrate, zinc sulfate heptahydrate, manganese II sulfate heptahydrate, chitin derived from natural sources and a bacteria of the Streptomyces griseus strain wherein the broth has a pH of about 7.0 adjusted with a solution for establishing and maintaining a pH of about 7.0, such as phosphoric acid can be intermixed with the basal broth in predetermined ratios by volume to form a pesticide or insecticide using the teachings of this invention. The chitinase broth can be used alone as an inhibitor for chitin-containing based fungi pests or insects or chitinase broth mixed in predetermined ratio by fluid volume with the basal broth to form a pesticide, an insecticide, a fungicide, or a biocide.

2. Description of the Prior Art

The achievement of human objectives is frequently dependent upon the use of chemical agent enabling means. However, the use of such chemical agent enabling means in many instances has associated therewith certain corresponding hazards, unknown or unwanted side effects or adverse consequences. As a result, the suitability of such chemical agent enabling means for practical application can be considered only after consideration of these hazards, and side effect adverse consequences.

By way of illustration, human history is replete with examples of human existence being directly or indirectly threatened by infestations of pests including particularly insects. A multiplicity of varieties of insects have constituted a more or less continual threat to the human food supply and, therefore, a menacing hazard to human existence. The explosive manner in which such lower life forms can reproduce in conducive circumstances has resulted, on occasion, in the development of vast infestations which consume virtually all plant life in their paths. Less consequential infestations are commonplace. Prior to the development of effective pesticides in the twentieth century, human existence was largely dependent for the control of such pests upon naturally occurring environmental phenomena unfavorable to the existence and reproduction of such pests.

Effective pesticides for treating, controlling and destroying pests have largely been dependent upon chemical substances which poison and thereby kill the pests, or otherwise interfere with their reproductive capabilities. Unfortunately, such pesticides have characteristically been, to some degree, toxic or hazardous to human beings as well. Traditionally, the means by which such adverse consequences were avoided was dependent upon avoiding human exposure to such toxic or hazardous pesticides during and for a period of time after the application thereof. It was believed, and with substantial scientific basis therefor, that avoidance of initial exposure to such pesticides allowed sufficient time for the pesticides to dissipate to such an extent or level as to no longer constitute a hazard to humans.

It has, however, more recently been discovered that there is a residual effect resulting from the use of pesticides, at least of certain types of pesticides. Adverse consequences can be experienced by humans long after the pesticides have been used or applied for treatment, control and killing of pests. In the case of such pesticides, the toxins can migrate through the soil into the water supply, or be absorbed into plant life which is eaten by humans or animals. Pesticide toxins or residues can be released into the atmosphere by evaporation, or other processes. These toxins or residues can remain in the environment as a hazard to humans and animals for as yet undetermined periods of time. As a consequence, many such pesticides have been banned by regulation and regulatory agencies, or are otherwise controlled in such a fashion that their utility has been partially or entirely lost.

Without the ability to use effective pesticides, human existence would again be dependent, to one degree or another, upon natural environmental controls. Such controls, as previously noted, are entirely insufficient to guarantee protection for the human food supply. Less significantly, but also worthy of mention, is the fact that in the twentieth century humans have been conditioned by experience to expect food which is free of pests including insects and the damage resulting therefrom. Accordingly food, which at one time in human history would have been entirely acceptable, is no longer considered even to be edible.

Still further, there are a multitude of other benefits to be derived from the control of pests. While these need not be enumerated, several are particularly worthy of note. The transmission of diseases and other animal and human maladies has long been known to be associated directly or indirectly with the existence of pests. Therefore, the ability to control pests is, in many cases, critical to the control of diseases. Similarly, certain varieties of pests themselves carry toxins hazardous to humans.

Further, none of the prior art discloses or teaches a chitinase broth having the composition disclosed herein which, as a chemical agent, when brought into contact with chitin-containing fungi, pests or insects acts as an inhibitor thereof.

Also, none of the prior art discloses or teaches a basal broth having the composition disclosed herein, or use of a basal broth having the composition disclosed herein as a pesticide, an insecticide, a fungicide, or a biocide.

In addition, none of the prior art discloses or teaches a mixture of the chitinase broth having the composition disclosed herein and the basal broth having the composition disclosed herein, the mixture forming a pesticide, an insecticide, a fungicide, or a biocide.

Further, none of the prior art discloses or teaches a basal broth having the composition disclosed herein, or use of a basal broth having the composition disclosed herein having a synergistic chemical fungicide for enhancing anti-fungal activity and using the same as a pesticide, an insecticide, a fungicide, or a biocide.

In certain applications involving treatment of plant material, such as grapevines, it is desirable to use a chitinase containing chemical agent which when brought into contact with chitin containing fungi or insects acts as an inhibitor thereof, thereby enhancing plant growth by biological control of plant pathogens.

It also is desirable to have a basal broth composition and a method for preparing and using the basal broth composition, the basal broth composition being operable to ensure that pests, including particularly insects, can be controlled and destroyed to such an extent that they no longer constitute a threat to the human food supply. In the present invention, the basal broth composition generally does not present a hazard or cause side effects or adverse consequences for humans and animals. The basal broth composition generally is not toxic to humans or animals even when coming into direct contact therewith and operates to eradicate a host of different varieties of pests, including particularly insects. The method of preparing the basal broth composition employs existing equipment without requiring equipment specifically adapted for the purpose. The composition can be applied in a broad range of strengths individually suited to specific pest or insect destroying objectives.

It is known in the art to use chitinase to inhibit fungi and insects that contain chitin and to enhance plant growth by biological control of plant pathogens. U.S. Pat No. 5,173,419 discloses two chitinases from Trichoderma harzianum P1 (ATCC 74058) which shows inhibition of chitin-containing fungi and insects. U.S. Pat. No. 5,173,419 also teaches that the chitinases can be applied to plants or to soil around plants which need protection from a chitinase containing pests.

U.S. Pat. No. 4,751,081 discloses a novel chitinase-producing bacteria strain for use for inhibiting chitinase-sensitive plant pathogens (fungi and nematodes).

U.S. Pat. No. 4,686,185 discloses the discovery and identification of a new species of micro-organism having an ability to produce chitinase, and the patent discloses a method of producing chitinase using the microorganism.

U.S. Pat. Nos. 3,862,007; 3,911,110; 4,751,081 and 4,940,840 disclose various methods of extracting chitinase, producing chitinase or using chitinase.

Standard known chemical fungicides, such as for example, Captan, Manzate, Chloroneb and Myclobutanil are used for treatment of fungi. The application rates of chemicals used are determined by the spectrum of activity of the particular chemical formulation of the chemical fungicide and the fungi under treatment.

Other known chemical fungicides are set forth in a reference entitled *FARM CHEMICAL HANDBOOK '95* Updated and Revised for '95, at pages F50 through F-73 (the "Chemical Fungicide Reference").

SUMMARY OF THE INVENTION

Therefore, it is an advantage of the present invention to provide a new novel and unique composition having a basal broth composition and a synergistic chemical fungicide having anti-fungi activity that when intermixed or combined with the basal broth or solution or composition of basal broth and chitin broth results in enhanced anti-fungal activity. Also, methods for preparing and using the compositions and solutions are disclosed and taught herein.

It is another advantage of the present invention to provide a new novel and unique basal broth composition and method for preparing and using the basal broth composition.

Another advantage is to provide such a basal broth composition and method for preparing and using same which can be employed dependably to control pests without hazard to humans or animals.

Another advantage is to provide such a basal broth composition and methods for preparing and using same which are particularly well suited to use for their insecticidal capabilities.

Another advantage is to provide such a basal broth composition which can be employed as a pesticide in a wide variety of environments to control the population of such pests and limit its growth.

Another advantage is to provide such a basal broth composition which is particularly well suited to the control of and destruction of insects by exterminating those insects which come into contact with the composition or to which the composition is applied, both those on and above the earth's surface and those occupying subsurface areas of the earth.

Another advantage is to provide a basal broth composition which can be employed as an insecticide for destroying insects of all sizes and varieties, including those of microscopic size.

Another advantage is to provide such a basal broth composition which presents minimal hazard to humans or animals, whether or not they come into direct contact therewith and without regard to the length of exposure thereto.

Another advantage is to provide such a basal broth composition which employs an active element for attacking the physical structure of the insects which come into contact with the composition or to which it is applied, causing death within a very short period of time.

Another advantage is to provide a method for preparing such a composition which permits such composition to be produced inexpensively and in such volumes as to be entirely practical for virtually universal usage.

Another advantage is to provide a method for preparing the composition which is safe to those practicing the method and which requires only the use of conventional equipment in the practice of the method.

Another advantage is to provide such a method for preparing the composition which can be so adjusted as to achieve the desired operational characteristics in the resulting composition.

Another advantage of this invention is to provide a novel chitinase composition which can be used alone or in combination with a basal broth composition.

Another advantage of this invention is to produce chitinase broth that has utility as an inhibitor for chitin-containing fungi, pests or insects and to enhance plant growth by biological control of plant pathogens.

Another advantage is to provide a method for application of the composition which can employ most devices and systems, conventional and otherwise, to achieve application of the composition so as to be employable in most environments.

Another advantage is to provide such a method of application which is operable to achieve placement of the composition in the particular area or areas desired for optimum operative effect.

Another advantage is to provide a method for testing the effectiveness of compositions having particular utility in testing the composition of the present invention.

Another advantage is to provide such a method for testing which is safe to those conducting the test, which does not produce toxic substances or otherwise present hazardous consequences and which is reliable in providing desired information.

Another advantage of the present invention is that the utility of the above compositions is for the control and suppression of disease and nematodes. Using the teachings of this invention, a number of products can be formulated, prepared and used for treatment of plants, crops and soil.

Further advantages are to provide an invention for the purposes described which is dependable, economical, and effective in accomplishing its intended purpose.

BRIEF DESCRIPTION OF THE DRAWINGS

The features, aspects and advantages of the present invention will be readily apparent when considered in light of the following description hereinafter, including the description of the preferred embodiment, and the drawing set forth herein which includes the following figures, all of which are presented by way of example only, and not of limitation, and all obvious modifications hereof are understood to be part of or within the scope of the disclosure set forth herein:

FIG. 3 is a pictorial, top plan view of a vineyard illustrating two embodiments of the method for applying the composition of the present invention;

FIG. 4 is a perspective view of a vessel employed in the practice of the method for testing of the present invention;

FIG. 7 is a chart showing the killing effect of basal broth and chitin broth alone and in various ratios by fluid volume.

DESCRIPTION OF THE PREFERRED EMBODIMENTS

Figure 1:
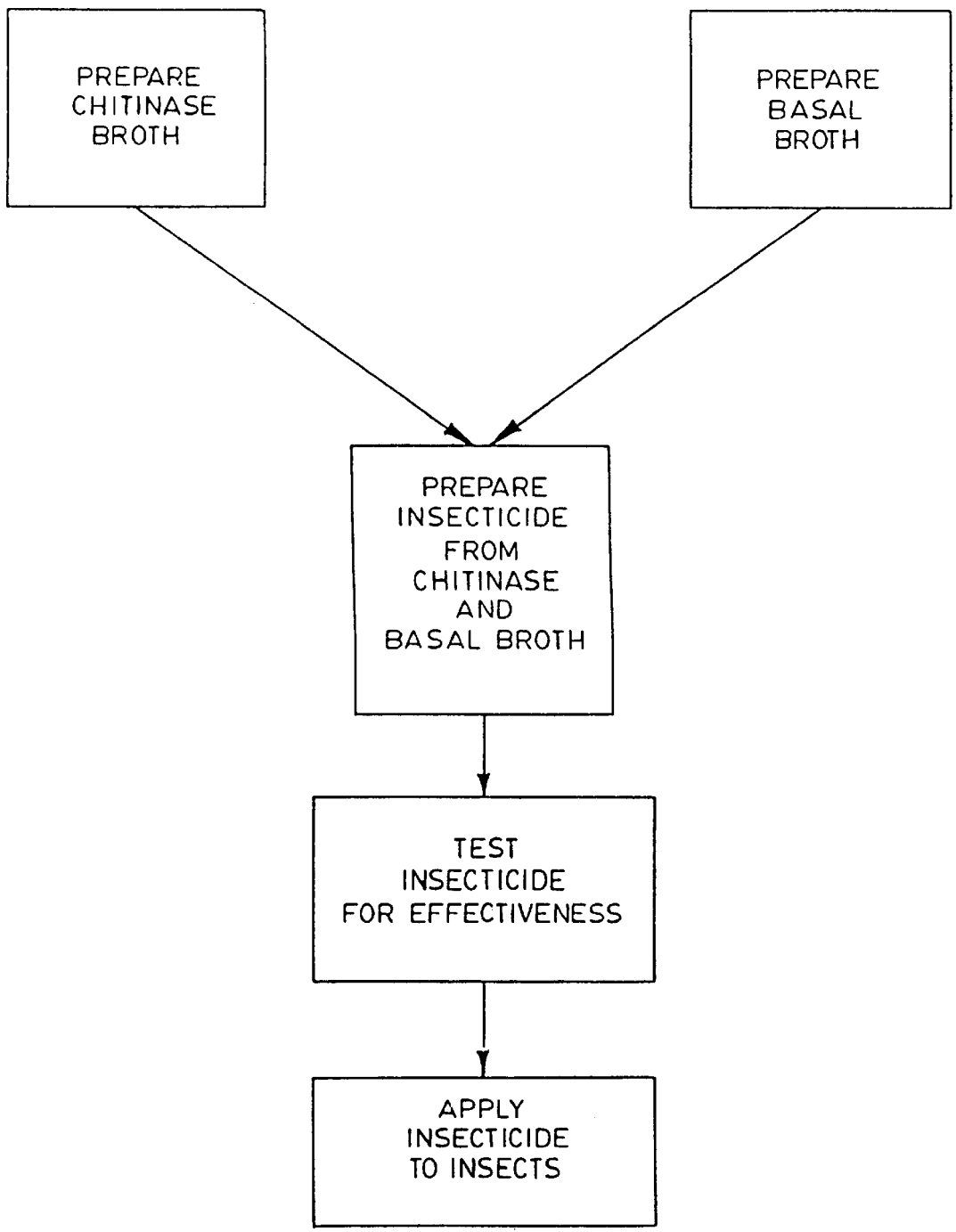
FIG. 1 is a schematic diagram depicting the method for preparing the composition of the preferred embodiment of the present invention.

Referring more particularly to the drawings, the basal broth and chitinase broth composition, method for preparing the same and method for testing the effectiveness thereof and application thereof as an insecticide, all of which comprise the preferred embodiment of the present invention, are illustrated diagrammatically in FIG. 1.

Composition And Method For Preparation Thereof

The method for preparing the composition of the preferred embodiment of present invention and the specific form of the resultant composition can be varied as to the volume produced, the ratio of the chemical components thereof, as well as with respect to the specific intended usage. The embodiments hereinafter described have specifically been adapted to the extermination of pests including insects. Pests are generally described as any destructive insect or other small animal or vermin. Insects are generally described as any of a group of small invertebrate that are more or less obviously segmented, including, but not limited to, spiders, centipedes, wood ticks, ticks, mites and the like.

More specifically, pests which constitute a threat to a wide variety of agricultural crops include those known in agriculture by their common names as leaf hoppers, mites, aphids, grape leaf skeletonizers, thrips, nematodes, phylloxera and the like as well as the eggs thereof. These insects are particularly a threat to such crops as cotton, grapes, and a variety of other commercial crops such as grown in the San Joaquin Valley of California, as well as in other locales. Nonetheless, while specifically adapted for usage as an insecticide against such insects, the present invention has been found operable as a pesticide or biocide against a host of other pests including various other insects.

The mechanism by which the composition of the present invention achieves its beneficial effect is due to a multifaceted, complex system and interaction of enzymes. While not necessary to an understanding of the composition and method for preparing or using of the composition, it is of illustrative benefit to first describe what appears to be the biochemical mechanism.

Figure 2:
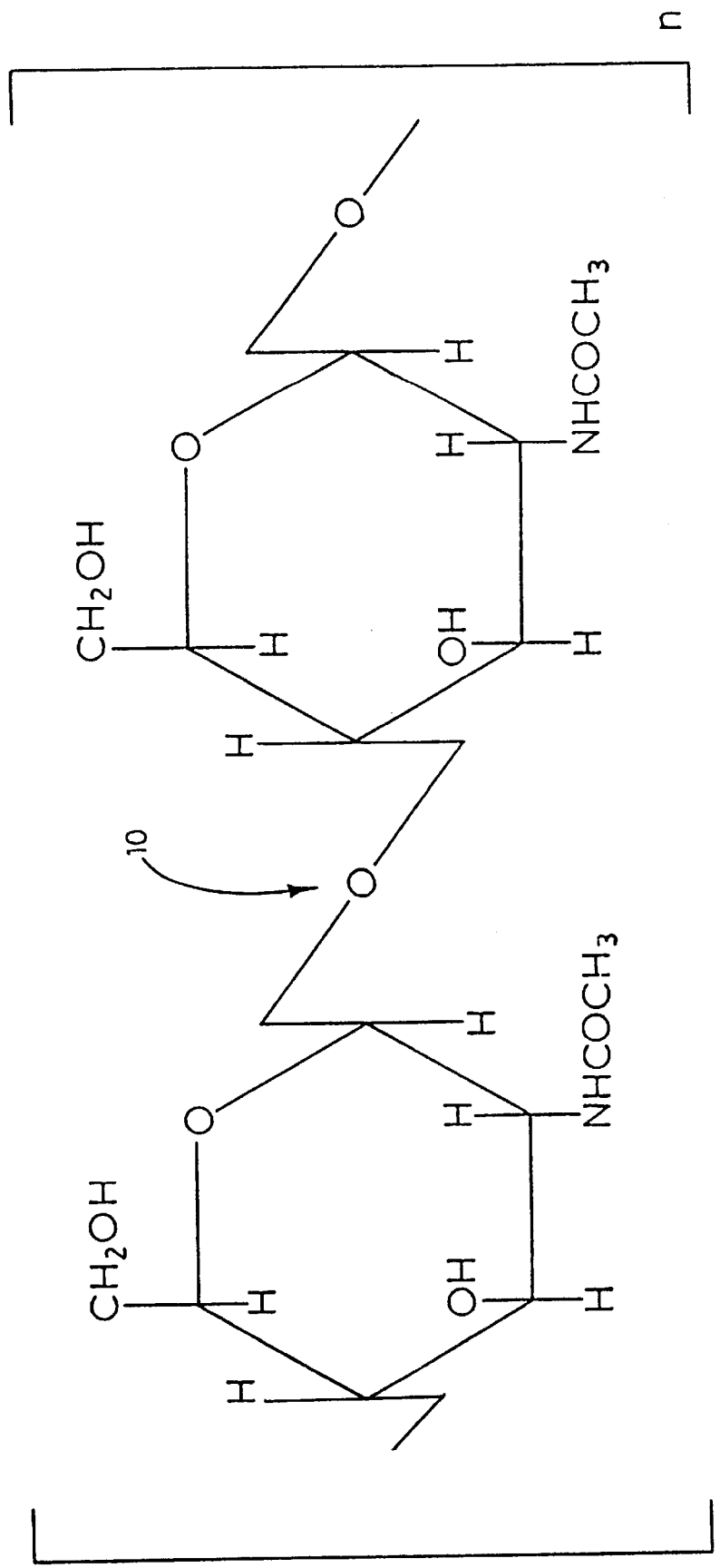
FIG. 2 shows the chemical structure for N-Acetyl-Glucosamine chain forming the exoskeleton of an insect showing the position at which the composition of the present invention is believed to cleave the chain.
Figure 5:
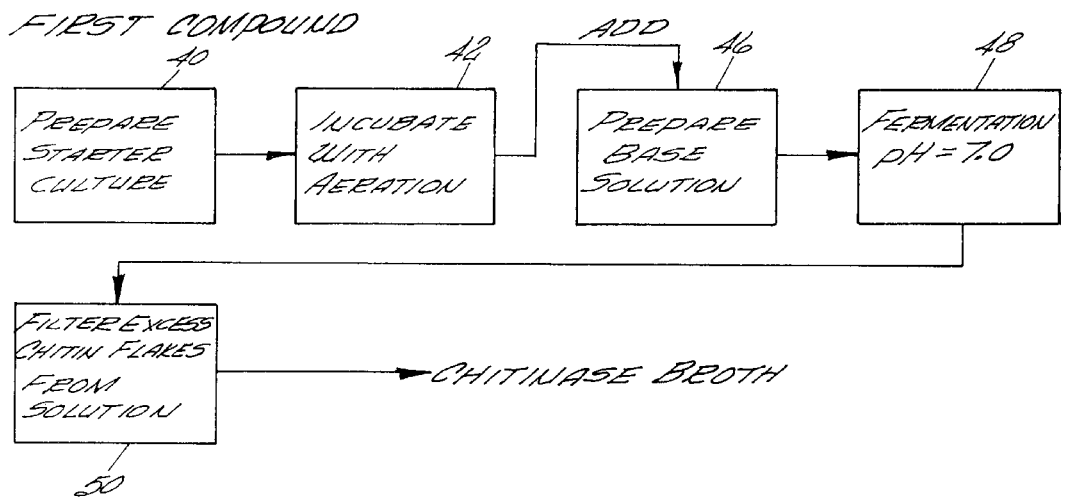
FIG. 5 is a block diagram showing the steps of a method for forming a chitinase broth.
Figure 6:
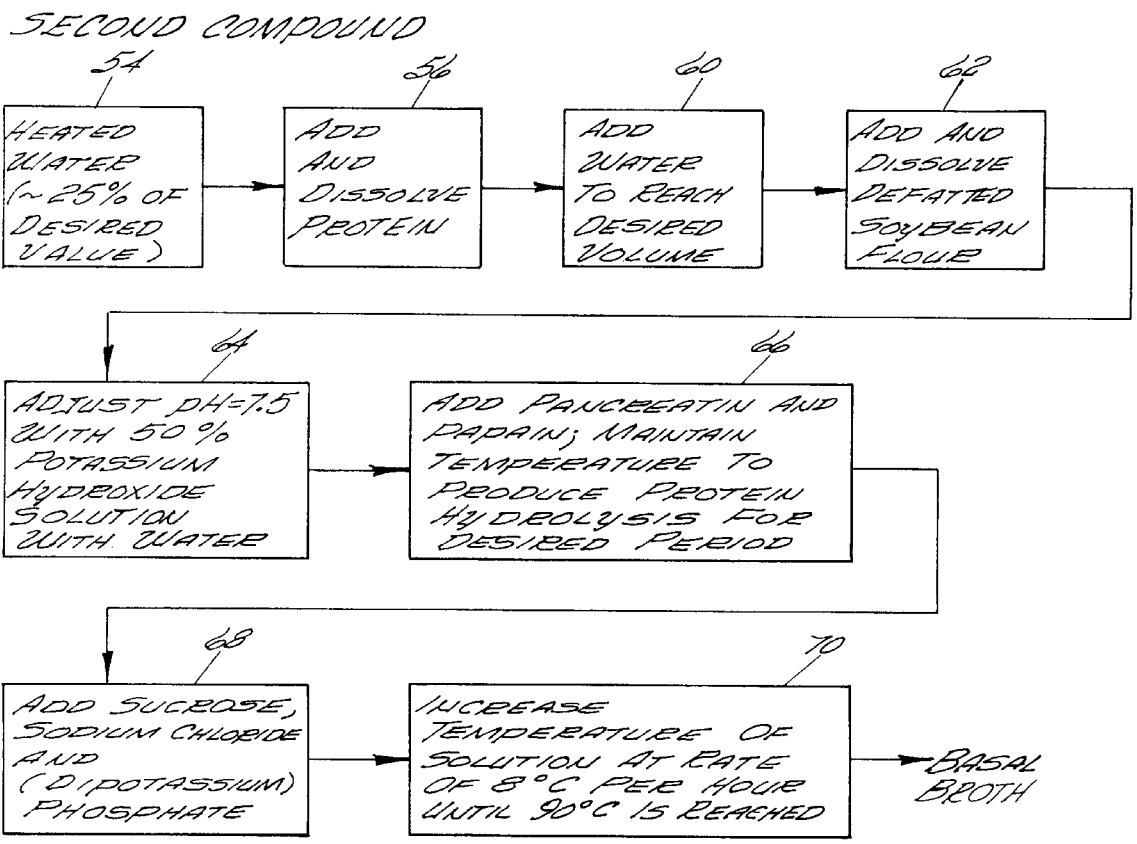
FIG. 6 is a block diagram showing the steps of a method for forming a basal broth.

In this regard, reference is made to the chemical structure represented diagrammatically in FIG. 2. The integuments, or exoskeleton, of many insects (including arachnids), crustaceans, and other invertebrates is composed of a chitin, a polysaccharide of N-acetyl-glucosamine having the structure shown in FIG. 2. The "n" in the structural formula indicates, as is the case, that this structure repeats itself to form long chains thereof. Chitin is also found in some fungi. It is believed that an active element contained in the composition of the present invention cleaves the carbon-oxygen bond at the position indicated by numeral 10 in FIG. 2. When this occurs, the structural integrity of the N-acetyl-glucosamine chain is undermined as is the structural integrity of the chitin-containing integuments of the insects. If the structural integrity of the chitin-containing integuments is undermined in this way, the insects (including arachnids), crustaceans, or other invertebrates will tend to lose their bodily fluids, leading eventually to death. Similarly, if the structure integrity of the chitin-containing fungi is undermined, the fungi's growth may be retarded or the fungi may eventually die. Experiments to date support the foregoing explanation of how the present invention and chitin interact, but it is entirely possible that other explanations individually, or in combination with the foregoing explanation, may turn out to be true. Irrespective of what the actual explanation is, the inventor has established by laboratory experiments, as well as field tests, that the results of the use of the present invention occur in the manner hereinafter to be described in greater detail.

Referring to FIG. 1, the basal broth composition and chitinase broth composition are mixed together in the preferred embodiment to form an insecticide. The first compound and the second compound can be referred to, for illustrative convenience, as "chitinase broth" and "basal broth", respectively. As previously noted, the insecticide can be formulated in batches of whatever volume is desired. The batch formulated in the practice of the method of the present invention, as described herein, is of a volume suited to commercial usage.

The chitinase broth is formulated, as described herein in accordance with the method of the present invention, in a 1,000 gallon batch. The substances, or materials, and the quantities thereof employed in the formulation of the chitinase broth are as follows:

1. about 3,000 grams of potassium phosphate, preferably dipotassium phosphate;
2. about 1,262 grams magnesium sulfate;
3. about 38 grams of iron sulfate, preferably iron (II) sulfate heptahydrate;
4. about 3.8 grams of zinc sulfate, preferably zinc sulfate heptahydrate;
5. about 3.8 grams of manganese sulfate, preferably manganese (II) sulfate monohydrate;
6. means for adjusting the pH, preferably about 400 grams of concentrated phosphoric acid, although those with ordinary skill in the art will know that other means for adjusting the pH can be used;
7. about 33 lbs. of chitin, preferably flaked chitin derived from crab shells;
8. 1,000 gallons of water; and
9. 2 liters of bacterial starter culture of the Streptomyces griseus strain that preferably has been maintained in pure culture.

The starter culture of Item 9 preferably is prepared by inoculating with the bacteria 2 liters of a base solution prepared using the above materials from items 1 through 8. This starter culture is preferably incubated with aeration for three days at approximately 72 degrees Fahrenheit.

The above-listed materials are, in the preferred embodiment of the invention, employed in the formulation of the chitinase broth as follows. The 1,000 gallons of water is preferably placed in a 1,500 gallon cone shaped, polypropylene tank, although those with ordinary skill in the art will know that other types of tanks can be used. Thereafter, the materials above-listed in items 1 through 5, 7 and 9 are added in any sequence. The tank preferably is equipped with an air blower that continuously pumps air through (i.e. aerates) the solution at ambient room temperature, which is about 25° C. to about 30° C. Those skilled in the art will know that aeration can be accomplished by numerous other means. Such aeration maintains the aerobic condition of the solution to that appropriate for fermentation. The pH of the solution is adjusted to about 7.0 by means known to those with ordinary skill in the art, such as by use of the addition of the necessary amount of concentrated phosphoric acid. Fermentation of the solution is allowed to proceed at ambient room temperature for a minimum of three days to as long as seven days. Upon completion of the fermentation process, the remaining chitin flakes, which have not been consumed in the solution, are preferably filtered out of the solution. The resulting brown liquid is the first compound referred to as "chitinase broth".

The basal broth is also formulated, in the preferred embodiment, in a 1,000 gallon batch. Those substances, or materials, and the quantities thereof required for formulation of the basal broth are as follows:

1. about 1,600 lbs. of protein concentrate, which preferably is dried sweet whey protein with thirty-four percent (34%) protein;
2. about 88 lbs. of flour, which preferably is defatted bakers soybean flour, having approximately fifty percent (50%) protein;
3. about 3,497 grams of pancreatin, preferably Porcine Pancreatin, 1× USP as defined by Sigma Chemical Co. of St. Louis, Mo.;
4. about 333 grams of papain, preferably crude papain, derived from papaya, and preferably 3× USP as defined by Sigma Chemical Co. of St. Louis, Mo., the papain being milled to pass through a 1 mm mesh screen;
5. about 100 lbs. of sugar, preferably sucrose;
6. about 132 lbs. of salt, preferably sodium chloride;
7. about 72 lbs. of potassium phosphate, preferably dipotassium phosphate;
8. means for adjusting the pH, preferably by a fifty percent (50%) solution potassium hydroxide with water, as hereinafter described, although those with ordinary skill in the art will know that other means for adjusting the pH can be used.

The device employed for the production of the basal broth preferably is a 1,500 gallon stainless steel milk holding tank. The tank is equipped with a paddle agitator. The jacket of the tank is wrapped with a continuous piece of copper tubing. Hot water having a temperature in the range of about 40° C. to about 90° C. produced by a boiler is circulated through the tubing to affect and control the temperature of the tank's contents.

Those with ordinary skill in the art will know that other types of tanks can be used, that means other than a paddle agitator can be used to mix the contents of the tank, and that means other than hot water circulating through copper tubing can be used to affect and control the temperature of the tank's contents.

Approximately 250 gallons of water are placed in the tank, and the boiler and agitator are activated. When the temperature of the water within the tank reaches about 40 degrees centigrade, the protein concentrate of Item 1 above is added and allowed to dissolve. Typically, four 50 lb. bags of the dried sweet whey protein concentrate are added at a time, and additional water is delivered into the tank with pressure to help in the dissolution of this material. This process is continued until all of the protein concentrate has been dissolved in the water and the resultant fluid volume of the solution within the tank has reached approximately 1,000 gallons. Next, the flour, preferably defatted soybean flour, is added to the solution and allowed to dissolve. The pH of the solution is adjusted to about 7.5 by means known to those with ordinary skill in the art such as the addition of the fifty percent (50%) potassium hydroxide solution with water. The pancreatin and papain are then added to the solution in any sequence. When the temperature of the solution within the tank reaches about 40 degrees centigrade, it is held at that temperature for two hours, during which time protein hydrolysis can occur in the solution. At the end of the two hours, the sugar (preferably sucrose), the salt (preferably sodium chloride) and, if desired, potassium phosphate (preferably dipotassium phosphate), are added to the solution in the tank. The temperature of the solution is then increased preferably at the rate of approximately 8 degrees centigrade per hour until the temperature of the solution reaches about 90 degrees centigrade (90° C.).

Preparation of the composition, or insecticide, of the preferred embodiment of present invention from the chitinase broth and the basal broth is then ready to be performed. In a typical production run, formulation of the chitinase broth is started on a first day. On the second day, production of the basal broth is begun. On the morning of the fourth day, the chitinase broth is mixed with an equal fluid volume of basal broth. The resultant mixture usually has a pH of about 7.0. Measurement of chitinase activity, by the test hereinafter set forth, usually shows no, or minimal, activity immediately after mixing of the chitinase broth and the basal broth. For example, the killing of a target insect, such as a grape leaf hopper nymph, by application of the composition at this point usually would take approximately ten minutes.

However, in accordance with the method of the present invention, the composition, or insecticide, is permitted to age or ferment. The composition preferably is permitted to age at an ambient temperature of about 40° C. to 50° C.

During this aging process, the pH of the composition usually drops to about 4.0 or lower. The desired range is a pH of about 5 to about 9 with about 7.0 being preferred. It has been discovered that such aging usually increases the activity of the active element and the time required to kill a leaf hopper nymph usually drops to approximately one minute. It is believed that this results from a secondary fermentation which occurs during aging and which increases the activity of the active element activity, although increases in the activity of the active element(s) may ultimately be explained in other ways. In any case, after such aging, the composition, or insecticide, is ready for further treatment.

The composition of equal fluid volume of basal broth to chitinase broth, a ratio of 1:1, is then preferably neutralized and autoclaved to increase the killing effect thereof.

The neutralization step is performed by adjusting the pH or the composition to be within the range of about 5 to about 9, with about 7.0 being desirable.

The autoclaving step is preferably performed by raising the temperature of the solution to about 120° C. under a pressure of about 15 lbs. psi for a period of about 15 minutes. The autoclaving usually results in the coagulation of the solution.

Using the above basal broth alone, chitinase broth alone and a mixture of basal broth and chitinase broth in a ratio of 1:1 by fluid volume, the following working examples were developed and tested.

EXAMPLE I

The following five (5) solutions were prepared in accordance with the above described "Composition and Method of Preparation Thereof" and were prepared for testing with the following treatments:

| Solution No. | Description | Treatment |
| --- | --- | --- |
| 1 | Equal parts by volume of chitin broth and basal broth | No secondary fermentation, no neutralization and no autoclaving |
| 2 | Equal parts by volume of chitin broth and basal broth | Secondary fermentation for 48 hours, neutralization and autoclaving |
| 3 | Basal broth | Neutralization and autoclaving |
| 4 | Chitin broth | Neutralization and autoclaving |
| 5 | Equal parts by volume of chitin broth and basal broth | Neutralization and autoclaving |

Each of the following solutions were added to vials having a minimum of 100 nematodes per 5 milliliter volume of solution in the following application rates:

| Test Volume No. | Microliters of Solution per vial |
| --- | --- |
| 1 | 000 |
| 2 | 005 |
| 3 | 050 |
| 4 | 500 |

Meloidogyne (root knot) nematodes were mixed with either 0, 5, 50 or 500 microliters of solution. In the following tests the phase "PRETREATMENT ALIVE" means number of nematodes alive prior to mixing with a solution. The phrase "48 HOUR ALIVE" means the number of nematodes alive 48 hours after mixing with a solution. The phase "48 HOUR DEAD" means the number of nematodes dead (or which appear to be substantially dead) 48 hours after mixing with the solution.

Upon mixing, the following treatments were performed.

TESTS OF SOLUTION NO. 1

SOLUTION TREATMENT NO. 1—PRETREATMENT SAMPLING & 48 HOUR TREATMENT SAMPLING MELOIDOGYNE (ROOT KNOT) NEMATODE COUNTS ARE 5 ml OF SOLUTION. RATES ARE MICROLITERS PER VIAL BASED ON A FINAL VOLUME OF 5 ml/TUBE.

| RATE/REP | PRETREATMENT ALIVE | 48 HOUR ALIVE | 48 HOUR DEAD |
| --- | --- | --- | --- |
| 000/1 | 116 | 114 | 2 |
| 000/2 | 131 | 128 | 3 |
| 000/3 | 164 | 164 | 0 |
| 000/4 | 148 | 147 | 1 |
| 000/5 | 120 | 120 | 0 |
| 000/6 | 109 | 107 | 2 |
| 005/1 | 111 | 79 | 32 |
| 005/2 | 134 | 130 | 4 |
| 005/3 | 128 | 125 | 3 |
| 005/4 | 144 | 116 | 28 |
| 005/5 | 142 | 98 | 44 |
| 005/6 | 130 | 126 | 2 |
| 050/1 | 130 | 0 | 130 |
| 050/2 | 129 | 0 | 129 |
| 050/3 | 140 | 0 | 140 |
| 050/4 | 119 | 0 | 119 |
| 050/5 | 136 | 0 | 136 |
| 050/6 | 133 | 0 | 133 |
| 500/1 | 111 | 0 | 111 |
| 500/2 | 119 | 0 | 119 |
| 500/3 | 122 | 0 | 122 |
| 500/4 | 116 | 0 | 116 |
| 500/5 | 127 | 0 | 127 |
| 500/6 | 120 | 0 | 120 |

The above test results show that the killing effect of Solution No. 1 was quite significant 48 hours after the nematodes were mixed with at least 50 microliters of Solution No. 1.

TESTS OF SOLUTION NO. 2

SOLUTION TREATMENT NO. 2—NEUTRALIZED AND AUTOCLAVED TREATMENT—PRETREATMENT SAMPLING & 48 HOUR TREATMENT SAMPLING MELOIDOGYNE (ROOT KNOT) NEMATODE COUNTS ARE 5 ml OF SOLUTION. RATES ARE MICROLITERS PER VIAL BASED ON A FINAL VOLUME OF 5 ml/TUBE.

| RATE/REP | PRETREATMENT ALIVE | 48 HOUR ALIVE | 48 HOUR DEAD |
| --- | --- | --- | --- |
| 000/1 | 118 | 118 | 0 |
| 000/2 | 160 | 156 | 5 |
| 000/3 | 144 | 141 | 3 |
| 000/4 | 113 | 113 | 0 |
| 000/5 | 147 | 144 | 3 |
| 000/6 | 148 | 146 | 2 |
| 005/1 | 112 | 110 | 2 |

-continued

| RATE/REP | PRETREATMENT ALIVE | 48 HOUR ALIVE | 48 HOUR DEAD |
|---|---|---|---|
| 005/2 | 113 | 110 | 3 |
| 005/3 | 109 | 103 | 6 |
| 005/4 | 134 | 131 | 3 |
| 005/5 | 123 | 120 | 3 |
| 005/6 | 125 | 68 | 57 |
| 050/1 | 127 | 0 | 127 |
| 050/2 | 143 | 0 | 143 |
| 050/3 | 127 | 0 | 127 |
| 050/4 | 131 | 0 | 131 |
| 050/5 | 150 | 0 | 150 |
| 050/6 | 131 | 0 | 131 |
| 500/1 | 134 | 0 | 134 |
| 500/2 | 119 | 0 | 119 |
| 500/3 | 111 | 0 | 111 |
| 500/4 | 131 | 0 | 131 |
| 500/5 | 109 | 0 | 109 |
| 500/6 | 122 | 0 | 122 |

The above test results show that the killing effect of Solution No. 2 was quite significant 48 hours after the nematodes were mixed with at least 50 microliters of Solution No. 2.

TESTS OF SOLUTION NO. 3

SOLUTION TREATMENT NO. 3—NEUTRALIZED AND AUTOCLAVED TREATMENT—PRETREATMENT SAMPLING & 48 HOUR TREATMENT SAMPLING

MELOIDOGYNE (ROOT KNOT) NEMATODE COUNTS ARE 5 ml OF RATES ARE MICROLITERS PER VIAL BASED ON A FINAL VOLUME OF 5 ml/TUBE SOLUTION.

RATES ARE MICROLITERS PER VIAL BASED ON A FINAL VOLUME OF 5 ml/TUBE.

| RATE/REP | PRETREATMENT ALIVE | 48 HOUR ALIVE | 48 HOUR DEAD |
|---|---|---|---|
| 000/1 | 122 | 122 | 0 |
| 000/2 | 136 | 135 | 1 |
| 000/3 | 133 | 130 | 3 |
| 000/4 | 161 | 160 | 1 |
| 000/5 | 118 | 118 | 0 |
| 000/6 | 135 | 135 | 0 |
| 005/1 | 155 | 152 | 2 |
| 005/2 | 155 | 154 | 1 |
| 005/3 | 125 | 123 | 2 |
| 005/4 | 133 | 129 | 4 |
| 005/5 | 140 | 135 | 5 |
| 005/6 | 153 | 149 | 4 |
| 050/1 | 132 | 0 | 132 |
| 050/2 | 127 | 0 | 127 |
| 050/3 | 141 | 0 | 141 |
| 050/4 | 130 | 0 | 130 |
| 050/5 | 129 | 0 | 129 |
| 050/6 | 125 | 0 | 125 |
| 500/1 | 130 | 0 | 130 |
| 500/2 | 133 | 0 | 133 |
| 500/3 | 125 | 0 | 125 |
| 500/4 | 129 | 0 | 129 |
| 500/5 | 119 | 0 | 119 |
| 500/6 | 121 | 0 | 121 |

The test results show that the killing effect of Solution No. 3 was quite significant 48 hours after the nematodes were mixed with at least 50 microliters of Solution No. 3.

TESTS OF SOLUTION NO. 4

SOLUTION TREATMENT NO. 4—NEUTRALIZED AND AUTOCLAVED TREATMENT—PRETREATMENT SAMPLING & 48 HOUR TREATMENT SAMPLING

MELOIDOGYNE (ROOT KNOT) NEMATODE COUNTS ARE 5 ml OF SOLUTION.

RATES ARE MICROLITERS PER VIAL BASED ON A FINAL VOLUME OF 5 ml/TUBE.

| RATE/REP | PRETREATMENT ALIVE | 48 HOUR ALIVE | 48 HOUR DEAD |
|---|---|---|---|
| 000/1 | 145 | 145 | 0 |
| 000/2 | 156 | 154 | 2 |
| 000/3 | 120 | 120 | 0 |
| 000/4 | 142 | 142 | 0 |
| 000/5 | 128 | 126 | 2 |
| 000/6 | 120 | 119 | 1 |
| 005/1 | 124 | 123 | 1 |
| 005/2 | 140 | 137 | 3 |
| 005/3 | 135 | 133 | 2 |
| 005/4 | 119 | 119 | 0 |
| 005/5 | 140 | 117 | 3 |
| 005/6 | 132 | 132 | 0 |
| 050/1 | 101 | 101 | 0 |
| 050/2 | 132 | 129 | 3 |
| 050/3 | 133 | 132 | 1 |
| 050/4 | 110 | 109 | 1 |
| 050/5 | 103 | 103 | 0 |
| 050/6 | 124 | 122 | 2 |
| 500/1 | 115 | 12 | 3 |
| 500/2 | 114 | 114 | 0 |
| 500/3 | 124 | 122 | 2 |
| 500/4 | 118 | 115 | 3 |
| 500/5 | 110 | 100 | 0 |
| 500/6 | 114 | 113 | 1 |

The above test results show that the killing effect of Solution No. 4 was quite limited 48 hours after the nematodes were mixed with either 0, 5, 50 or 500 microliters of Solution No. 4.

This example supports the understanding that chitinase broth alone does not appear to have independent killing effect and functions as a chemical agent inhibitor for chitinase-containing fungus and insects. Thus, the inhibiting effect of the chitinase broth clearly enhances the killing effect of the basil broth as supported by the other examples.

TESTS OF SOLUTION NO. 5

SOLUTION TREATMENT NO. 5—NEUTRALIZED AND AUTOCLAVED TREATMENT—PRETREATMENT SAMPLING & 48 HOUR TREATMENT SAMPLING

MELOIDOGYNE (ROOT KNOT) NEMATODE COUNTS ARE 5 ml OF SOLUTION.

RATES ARE MICROLITERS PER VIAL BASED ON A FINAL VOLUME OF 5 ml/TUBE.

| RATE/REP | PRETREATMENT ALIVE | 48 HOUR ALIVE | 48 HOUR DEAD |
|---|---|---|---|
| 000/1 | 116 | 115 | 1 |
| 000/2 | 132 | 131 | 1 |
| 000/3 | 150 | 150 | 0 |
| 000/4 | 142 | 139 | 3 |
| 000/5 | 146 | 145 | 1 |
| 000/6 | 110 | 110 | 0 |
| 005/1 | 143 | 37 | 106 |
| 005/2 | 132 | 110 | 22 |
| 005/3 | 132 | 28 | 104 |
| 005/4 | 135 | 115 | 20 |
| 005/5 | 118 | 108 | 10 |

-continued

| RATE/REP | PRETREATMENT ALIVE | 48 HOUR ALIVE | 48 HOUR DEAD |
|---|---|---|---|
| 005/6 | 120 | 100 | 20 |
| 050/1 | 125 | 0 | 125 |
| 050/2 | 122 | 0 | 122 |
| 050/3 | 120 | 0 | 120 |
| 050/4 | 119 | 0 | 119 |
| 050/5 | 140 | 0 | 140 |
| 050/6 | 134 | 0 | 134 |
| 500/1 | 130 | 0 | 130 |
| 500/2 | 129 | 0 | 129 |
| 500/3 | 118 | 0 | 118 |
| 500/4 | 136 | 0 | 136 |
| 500/5 | 129 | 0 | 129 |
| 500/6 | 130 | 0 | 130 |

The above test results show that the killing effect of Solution No. 5 was quite significant 48 hours after the nematodes were mixed with at least 50 microliters of Solution No. 5.

EXAMPLE 2

The following examples are repeat of Example 1 with the additional step of washing the samples with water after the 48 hour treatment.

EXAMPLE 2-ADDITIONAL TESTS OF SOLUTION NO. 1

SOLUTION TREATMENT NO. 1—PRETREATMENT SAMPLING & WASHED AFTER 48 HOUR TREATMENT SAMPLING

MELOIDOGYNE (ROOT KNOT) NEMATODE COUNTS ARE 5 ml OF SOLUTION. RATES ARE MICROLITERS PER VIAL BASED ON A FINAL VOLUME OF 5 ml/TUBE.

| RATE/REP | PRETREATMENT ALIVE | WASHED ALIVE | WASHED DEAD |
|---|---|---|---|
| 000/1 | 110 | 106 | 4 |
| 000/2 | 120 | 119 | 1 |
| 000/3 | 158 | 158 | 0 |
| 000/4 | 135 | 135 | 0 |
| 000/5 | 113 | 111 | 2 |
| 000/6 | 101 | 199 | 2 |
| 005/1 | 105 | 103 | 2 |
| 005/2 | 123 | 122 | 1 |
| 005/3 | 112 | 109 | 3 |
| 005/4 | 130 | 130 | 0 |
| 005/5 | 131 | 130 | 1 |
| 005/6 | 124 | 120 | 4 |
| 050/1 | 124 | 119 | 5 |
| 050/2 | 121 | 115 | 6 |
| 050/3 | 124 | 121 | 3 |
| 050/4 | 113 | 110 | 3 |
| 050/5 | 127 | 123 | 4 |
| 050/6 | 121 | 121 | 0 |
| 500/1 | 104 | 8 | 96 |
| 500/2 | 114 | 20 | 94 |
| 500/3 | 112 | 25 | 87 |
| 500/4 | 101 | 17 | 84 |
| 500/5 | 116 | 19 | 97 |
| 500/6 | 114 | 26 | 88 |

The above test results show that the killing effect of Solution No. 1 was quite significant 48 hours after the nematodes were mixed with at least 500 microliters of Solution No. 1 and after the nematodes were washed with water.

EXAMPLE 2-ADDITIONAL TESTS OF SOLUTION NO. 2

SOLUTION TREATMENT NO. 2—NEUTRALIZED AND AUTOCLAVED TREATMENT—PRETREATMENT SAMPLING & WASHED AFTER 48 HOUR TREATMENT SAMPLING

MELOIDOGYNE (ROOT KNOT) NEMATODE COUNTS ARE 5 ml OF SOLUTION.

RATES ARE MICROLITERS PER VIAL BASED ON A FINAL VOLUME OF 5 ml/TUBE.

| RATE/REP | PRETREATMENT ALIVE | WASHED ALIVE | WASHED DEAD |
|---|---|---|---|
| 000/1 | 107 | 106 | 1 |
| 000/2 | 145 | 143 | 2 |
| 000/3 | 135 | 135 | 0 |
| 000/4 | 110 | 110 | 0 |
| 000/5 | 136 | 132 | 4 |
| 000/6 | 140 | 139 | 1 |
| 005/1 | 102 | 100 | 2 |
| 005/2 | 100 | 99 | 1 |
| 005/3 | 96 | 94 | 2 |
| 005/4 | 125 | 119 | 6 |
| 005/5 | 118 | 113 | 5 |
| 005/6 | 112 | 103 | 9 |
| 050/1 | 120 | 118 | 2 |
| 050/2 | 134 | 130 | 4 |
| 050/3 | 119 | 116 | 3 |
| 050/4 | 128 | 119 | 9 |
| 050/5 | 139 | 139 | 0 |
| 050/6 | 115 | 112 | 3 |
| 500/1 | 122 | 12 | 110 |
| 500/2 | 106 | 40 | 66 |
| 500/3 | 100 | 20 | 80 |
| 500/4 | 122 | 22 | 100 |
| 500/5 | 95 | 11 | 84 |
| 500/6 | 112 | 24 | 88 |

The above test results show that the killing effect was quite significant 48 hours after the nematodes were mixed with at least 500 microliters of Solution No. 2.

EXAMPLE 2-ADDITIONAL TESTS OF SOLUTION NO. 3

SOLUTION TREATMENT NO. 3—NEUTRALIZED AND AUTOCLAVED TREATMENT—PRETREATMENT SAMPLING & WASHED AFTER 48 HOUR TREATMENT SAMPLING

MELOIDOGYNE (ROOT KNOT) NEMATODE COUNTS ARE 5 ml OF SOLUTION.

RATES ARE MICROLITERS PER VIAL BASED ON A FINAL VOLUME OF 5 ml/TUBE.

| RATE/REP | PRETREATMENT ALIVE | WASHED ALIVE | WASHED DEAD |
|---|---|---|---|
| 005/1 | 138 | 135 | 3 |
| 005/2 | 142 | 139 | 3 |
| 005/3 | 113 | 109 | 4 |
| 005/4 | 119 | 115 | 4 |
| 005/5 | 128 | 122 | 6 |
| 005/6 | 139 | 137 | 2 |
| 050/1 | 124 | 121 | 3 |
| 050/2 | 115 | 109 | 6 |
| 050/3 | 132 | 128 | 4 |
| 050/4 | 119 | 118 | 1 |
| 050/5 | 117 | 114 | 3 |
| 050/6 | 114 | 111 | 3 |
| 500/1 | 128 | 112 | 16 |

-continued

| RATE/REP | PRETREATMENT ALIVE | WASHED ALIVE | WASHED DEAD |
| --- | --- | --- | --- |
| 500/2 | 123 | 104 | 19 |
| 500/3 | 114 | 94 | 20 |
| 500/4 | 117 | 77 | 40 |
| 500/5 | 110 | 94 | 16 |
| 500/6 | 117 | 103 | 14 |

The above test results show that the killing effect of Solution No. 3 was quite significant 48 hours after the nematodes were mixed with at least 500 microliters of Solution No. 3. Therefore, it appears that the desired killing effectiveness at the higher concentration can be substantially maintained by avoiding washing of the insects for a sufficient period of time to allow the insects to completely die.

EXAMPLE 2-ADDITIONAL TESTS OF SOLUTION NO. 4

SOLUTION TREATMENT NO. 4—NEUTRALIZED AND AUTOCLAVED TREATMENT—
PRETREATMENT SAMPLING & WASHED AFTER 48 HOUR TREATMENT SAMPLING
MELOIDOGYNE (ROOT KNOT) NEMATODE COUNTS ARE 5 ml OF SOLUTION.
RATES ARE MICROLITERS PER VIAL BASED ON A FINAL VOLUME OF 5 ml/TUBE.

| RATE/REP | PRETREATMENT ALIVE | WASHED ALIVE | WASHED DEAD |
| --- | --- | --- | --- |
| 000/1 | 136 | 136 | 0 |
| 000/2 | 150 | 150 | 0 |
| 000/3 | 110 | 106 | 4 |
| 000/4 | 138 | 136 | 2 |
| 000/5 | 125 | 123 | 2 |
| 000/6 | 109 | 109 | 0 |
| 005/1 | 112 | 109 | 3 |
| 005/2 | 127 | 121 | 6 |
| 005/3 | 124 | 120 | 4 |
| 005/4 | 110 | 110 | 0 |
| 005/5 | 125 | 119 | 6 |
| 005/6 | 119 | 118 | 1 |
| 050/1 | 85 | 84 | 1 |
| 050/2 | 122 | 117 | 5 |
| 050/3 | 125 | 122 | 3 |
| 050/4 | 97 | 94 | 3 |
| 050/5 | 82 | 80 | 2 |
| 050/6 | 121 | 116 | 5 |
| 500/1 | 105 | 101 | 4 |
| 500/2 | 101 | 100 | 1 |
| 500/3 | 119 | 115 | 4 |
| 500/4 | 100 | 97 | 3 |
| 500/5 | 96 | 94 | 2 |
| 500/6 | 110 | 106 | 4 |

This above test results show that the killing effect of Solution No. 4 was quite limited 48 hours after the nematodes were mixed with either 0, 5, 50 or 500 microliters of Solution No. 4 and after the nematodes were washed with water.

The above appears to show that the chitinase broth functions as a chemical agent inhibitor for chitin-containing fungi and insects. Thus, the inhibitor effect of the chitinase broth would enhance the killing effect of the basal broth as supported by the other examples.

EXAMPLE 2-ADDITIONAL TESTS OF SOLUTION NO. 5

SOLUTION TREATMENT NO. 5—NEUTRALIZED AND AUTOCLAVED TREATMENT—
PRETREATMENT SAMPLING & WASHED AFTER 48 HOUR TREATMENT SAMPLING
MELOIDOGYNE (ROOT KNOT) NEMATODE COUNTS ARE 5 ml OF SOLUTION.
RATES ARE MICROLITERS PER VIAL BASED ON A FINAL VOLUME OF 5 ml/TUBE.

| RATE/REP | PRETREATMENT ALIVE | WASHED ALIVE | WASHED DEAD |
| --- | --- | --- | --- |
| 000/1 | 111 | 109 | 2 |
| 000/2 | 122 | 120 | 2 |
| 000/3 | 135 | 135 | 0 |
| 000/4 | 138 | 137 | 1 |
| 000/5 | 140 | 140 | 0 |
| 000/6 | 105 | 105 | 0 |
| 005/1 | 133 | 127 | 6 |
| 005/2 | 117 | 114 | 3 |
| 005/3 | 123 | 120 | 3 |
| 005/4 | 132 | 127 | 5 |
| 005/5 | 104 | 104 | 0 |
| 005/6 | 113 | 111 | 2 |
| 050/1 | 119 | 113 | 6 |
| 050/2 | 108 | 103 | 5 |
| 050/3 | 104 | 103 | 1 |
| 050/4 | 107 | 103 | 4 |
| 050/5 | 121 | 118 | 3 |
| 050/6 | 129 | 128 | 1 |
| 500/1 | 120 | 118 | 2 |
| 500/2 | 115 | 102 | 13 |
| 500/3 | 108 | 103 | 5 |
| 500/4 | 130 | 120 | 10 |
| 500/5 | 121 | 115 | 6 |
| 500/6 | 119 | 112 | 7 |

The above test results show that the killing effect of Solution No. 5 was quite limited 48 hours after the nematodes were mixed with either 0, 5, 50 or 500 microliters of Solution No. 5 and after the nematodes were washed with water.

In conclusion, when the basal broth composition is used or the combined basal broth and chitinase broth composition is used in a field application, irrigation of the field should be stopped for at least 48 hours to avoid undermining the killing effect of the pesticide and enhance the likelihood that the pests (including insects) will be destroyed by dehydration.

Method For Testing The Effectiveness Of The Composition

Once preparation of the composition has been completed, it can be tested for effectiveness practicing the method for testing the effectiveness thereof of the present invention. Such testing is of advantage, for reasons which will be noted, but not required for practicing of the present invention.

The conventional test, or assay, for the active element activity of the present invention does not work with a matrix of the composition due to the presence of sugars in the composition. However, the method for testing of the present invention does work. In accordance with the method of the present invention, highly purified powdered chitin is sieved through a 400 mesh screen. The resulting test substance; that is, sieved, purified powdered chitin, is mixed with a solution composed of chitinase broth, absent the flaked chitin of that formulation. In place of the flaked chitin, 150 mg of the sieved, purified powdered chitin is used per 100 cc medium. Thereafter, 2.0 grams of agar is added to the solution and the solution is heated in an autoclave at 121 degrees centigrade for fifteen minutes. The resulting solution is allowed to cool and dispensed into petri dishes. Each petri dish is preferably of a size having a diameter of 49 mm and a depth of 5 mm. The solution is permitted to cool further and to solidify.

Subsequently, a well is prepared in the center of the plate by aspirating a 6 mm diameter plug of the solid agar using a straw, or the like. The well is then filled with three drops of the basal broth and chitinase broth composition, or insecticide, to be tested for effectiveness. In other words, the purpose for the test is to measure the extent of the active element activity in the composition. One hour is allowed to elapse. During this period of time, the three drops of the composition to be tested changes from opaque to transparent in a certain zone or area thereof. The size of the area of this zone of clearing at the end of one hour is then measured. This measurement serves as an index of the active element activity in the composition being tested. Typical zones of clearing are 10 to 14 mm.

The test of the present invention is illustrated in FIG. 4 wherein a petri dish 40 has a bottom wall 41 and a cylindrical side wall 42. The side wall has a circular upper peripheral edge 43 and, with the bottom wall, defines a receptacle 44. The test medium consisting of agar and chitinase broth absent flaked chitin but, instead, containing the sieved, purified powdered chitin in solidified form is indicated at 45 within the receptacle. The test medium has an upper surface 46. The well formed in the test medium is indicated at 47. The three drops of compound to be tested constitutes a test quantity 48 having an upper surface 49 within which the zone of clearing appears and can be measured, as previously described.

Method For Applying The Composition

The method for application of the composition of the present invention can take a variety of different forms depending upon the specific form or forms of pests to be controlled and the environment, or domain, thereof. There are two domains habitated by plant pests. The first domain is the soil. The second domain is above ground in the fruit and foliage of the plants.

In the first or soil domain, the composition of the present invention has been employed in killing parasitic nematodes and the grape root aphid phylloxera, as well as their eggs. For nematode and phylloxera control in grapevines, the following methods have been used. For illustrative convenience in this regard, attention is directed to FIG. 3. As shown therein, a vineyard is composed of rows of grapevines 20 individually contain a plurality of grapevines 21. Adjacent rows of grapevines are spaced from each other by an avenue, or path, 22. The vineyard has a drip irrigation system 23 composed of a drip irrigation line 24 individual to each row of grapevines. Each of the drip irrigation lines mounts a plurality of drip irrigation emitters 25 through which irrigation water is released by drip irrigation in the conventional manner.

As will be referred to in relation to another embodiment of the method for application of the composition, a tractor 30 mounts a conventional spray device 31 having oppositely directed spray heads 32.

In a first embodiment of the method of application of the present invention employed relative to the soil domain, the composition is injected into drip irrigation system 23 at the rate of 10 gallons per acre. The composition is metered into the drip irrigation system at the initiation of irrigation and such metering is controlled by a conventional venturi injection system. The drip period following injection varies with soil type and drip system water volumes, but in all cases sufficient water is applied to saturate the soil to a depth of 18 to 24 inches. This is the area of the soil occupied by the roots and habitated by the target pests.

With this method of application, the populations of root knot, citrus, lesion, daggar, ring, spiral and pin nematodes, as well as their respective eggs, have been reduced by seventy percent (70%) to one hundred percent (100%) in fifteen days. It is clear that the killing effect is increased if no water is applied for about 3 to about 7 days to enable the synergism of the multifaceted system to function effectively. In fact, this is true for all species of nematodes. Dramatic reductions in phylloxera, as evidenced by laboratory and visual root inspections, have also been achieved. In addition, enhanced growth of the roots and canopies of the grapevines is commonly observed as the result of this method of application which is believed attributed to or enhanced by the inhibiting effect of the chitinase broth on chitin-containing fungi and insects.

In a second embodiment of the method of application, 10 to 20 gallons of the composition per acre have been applied either to the vineyard floor or injected with shanks into the soil and flood irrigated to a depth of 18 to 24 inches. Significant nematode and phylloxera reductions were achieved.

In still other embodiments, 10 to 20 gallons of the composition per acre have been applied to the soil surface in vineyards and taken into the soil with rain; 10 to 20 gallons of the composition per acre have been applied with overhead sprinklers in vineyards; and 10 to 20 gallons of the composition per acre have been metered into the irrigation water released to the vineyard in a normal water run method of application.

In summary, all conventional methods of irrigation used in commercial grape vineyards have been used with positive results. Nematode and phylloxera populations have been suppressed with enhanced root and canopy growth in the grapevines. The composition can be applied in the spring, fall and summer. This is unique in that currently available conventional pesticides must be applied well in advance of harvest in order to avoid the presence of toxic pesticide residues in the fruit. Since the composition of the present invention is not toxic to humans, animals or the environment, the time for application is dependent solely upon considerations regarding the most opportune time to control the pests.

The following embodiments of the method of application have been used for vegetable crops, including carrots, potatoes, beets and lettuce. The composition is applied at the rate of 10 gallons per acre which is shanked into the planting bed before, during and after planting followed by furrow irrigation and water run later in the season as needed. Total volume of the composition applied per season is from 10 to 40 gallons. In another embodiment, 10 gallons of the composition per acre is applied through overhead sprinklers after planting and through later irrigations on the growing crops. The total volume of the composition applied per season is again from 10 through 40 gallons.

The composition has also been applied with preirrigation water to vegetable crops. The crops are planted in June and July. Soil samples taken in August and October show zero nematode counts. The crops have been harvested and no nematode damage has been noted. In previous growing seasons, the same fields have had between twenty-five percent (25%) and one hundred percent (100%) crop loss due to nematode damage.

Equivalent results have been obtained with citrus, walnut and stone fruit crops using these methods of application.

Embodiments of the method of application have also been employed in the second domain of such insects; that is, above ground. Experiments to date have been performed on grape leaf hoppers, a variety of mites and aphids, thrips and white flies and their eggs. It is believed that, because of the herein suggested biochemical explanation for the operation of the composition in the killing of insects, the composition should make contact with the target insects. It will be recalled that this proposed biochemical explanation involves the hydrolysis of the insect, or their eggs, and takes place as a result of the active element present in the composition making contact with the exoskeletons of the insects. Accordingly, complete coverage of the insect should occur.

In a typical above ground application for insects, it has been observed that the composition works quickly and most effectively when applied without dilution. However, this is not cost effective. The maximum dilution rate that yields acceptable killer rate is about one part composition to three parts water. It has also been observed that, in the case of application of the material by spray, the smaller the particle size of aerosol produced, the greater the insecticidal activity. The particle size is reduced with a surfactant, such as cottonseed oil, and the dilute composition and surfactant delivered with conventional spray devices that move large volumes of air, such as indicated at 31 in FIG. 3. In addition, the longer the target insect remains wet in such contact, the better the kill. Accordingly, applications at night or early morning, when ambient temperatures are low and dew potential higher, are more effective.

In a typical foliar application, it is first determined what volume of water is sufficient to achieve complete wetting of both sides of the leaf per acre of crop. The composition is then diluted at the rate of one part of composition to four parts water in the desired volume, one quart of cottonseed oil is added per 100 gallons of final volume. The solution is mixed well and applied to the crop with a spray device, such as spray device 31. As an example, it has been determined that 50 gallons of the mixture delivered in a "Fan Jet" spray device was sufficient to cover an acre of "Flame" table grapes. In a specific test, 12.5 gallons of the composition were added to 37.5 gallons water and 1 pint cottonseed oil. Twenty-four hours after application, there was an eighty-five percent (85%) reduction in the grape leaf hopper nymph population and a fifty percent (50%) reduction in flying adult grape leaf hopper nymph population.

Generic Method of Preparing Chitinase Broth

The preferred embodiment for preparation of the chitinase broth has been described above.

The generic method for preparing the chitinase broth of the present invention is shown by the block diagram of FIG. 5. This is labeled as the first compound in FIG. 5. The method comprises the step of preparing a starter culture shown as 40. The starter culture includes a starter or base solution and a bacterial culture of the Streptomyces griseus strain in pure culture. The starter solution is preferably a base solution of the chitinase broth without the bacterial culture. The starter culture is incubated with aeration shown by 42, for a predetermined period of time at ambient temperature.

The base solution is prepared, as shown by 46, by mixing in an aerobic condition a predetermined quantity of water by volume, a selected quantity by weight of magnesium sulfate, iron (II) sulfate and sulfate heptahydrate, trace amounts of zinc sulfate heptahydrate and manganese sulfate monohydrate and a copious supply of chitin derived from natural sources. Thereafter, a sufficient quantity of the starter culture is added to the base solution to cause fermentation at ambient temperatures. The pH of the mixture of starter culture and base solution has its pH level adjusted to about 7.0 by use of a means for adjusting the pH, such as by the addition of an appropriate quantity of concentrated phosphoric acid. The mixture is then subject to the step of fermentation as shown by 46. The step of fermentation occurs for a period of days, for example about 3 days to about 7 days. Upon completion of the step of fermentation, the step of filtering the mixture to remove the chitin remaining after the fermentation process is performed as shown by 50. The resulting solution is brown in color and is referred to as the "chitinase broth Broth".

Generic Method of Preparing Basal Broth

FIG. 6 is a block diagram showing the method for preparing the second compound referred to as the basal broth.

The method for preparing the basal broth comprises the steps of heating a predetermined volume of water which is less than a desired volume of water to a temperature of about 40° C. as shown by 54, and dissolving in the water a selected quantity of protein concentrate having about fifty percent (50%) protein as shown by 56. During the heating and dissolving, the next step is adding additional water to raise the volume of water to the desired volume, as shown by 60. Thereafter, flour, such as a defatted soybean flour, having a selected percentage of protein is added to the desired volume of solution, as shown by 62. The pH of the solution is adjusted in a range of about 5 to about 9, with a level of about 7.0 being preferred, by using known means for adjusting the pH, such as by adding an appropriate amount of a fifty percent (50%) potassium hydroxide solution with water, as shown by 64.

The next step is adding enzymes to the solution comprising pancreation and papain and maintaining the solution at a sufficient temperature to produce protein hydroylsis for a desired period of time, as illustrated by 66. Pancreation is a cream colored amorphous powder obtained from the fresh pancrea of a hog which contains amylopsin, trypsin, steapsin and other enzymes. Papain is an enzyme preparation obtained from the juice of the fruit and leaves of papaya (Carcia papaya) and contains proteolytic enzymes.

Upon completion of the protein hydroylsis step, predetermined quantities of sugar (such as sucrose), salt (such as sodium chloride) and potassium phosphate (such as dipotassium phosphate) are added to the solution in any sequence, as shown by 68. The temperature of the solution is increased at a selected rate per hour until a desired high temperature in the order of 90° C. is reached, as shown by 70.

The pH of the solution is preferably adjusted to be in the range of about 5 to about 9 and can be adjusted to a level of about 7 by using well known means for adjusting the pH of the solution, such as for example, a solution of fifty percent (50%) potassium hydroxide.

The chart of FIG. 7 shows the results of tests based on the first compound and second compound, alone, and for mixtures thereof in various ratios by fluid volume. Tests 1, 2 and 3 are actual based on the earlier examples provided herein. Tests 4 and 5 are extrapolated results based on actual results.

Test 1 shows that the chitinase broth alone has a low killing effect on fungus and nematodes. However, the chitinase basal functions as an inhibitor for chitin-containing fungi pests and insects.

Test 2 shows that the basal broth alone has a high killing effect on fungi, nematodes, pests and insects.

Test 3 shows that a mixture of chitinase broth, and basal broth, having a ratio of 1:1 by volume, has a high killing effect on pests and insects. This is due to the synergism that develops from the complex multifaceted biochemical system. One part of this complex mechanism is that the chitinase appears to influence the native soil in the vicinity of the plant upon which is applied to cause enzyme action to increase.

Tests 4 and 5 represent the extrapolation of the 1:1 ratio and shows that as the ratio of basal broth is diluted from 1:1, the killing effect appears to decrease. By changing the chitinase broth to basal broth ratio to a 1:2 ratio, a medium killing effect is obtained. When the chitinase broth to basal broth ratio is changed to a 2:1 ratio, the killing effect decreases to a low-medium range.

In summary, the present invention shows broad utility in the control of both above and below ground plant pests including insects. In both domains, the principal mode of action appears to be the hydrolysis of the chitin in the shell of the egg, nymphs and adults caused by the small molecule, water soluble compounds in the composition. Many of the plant pathogenic fungi are known to contain chitin in their somatic structures so that control of these chitin-containing fungi is also believed possible. In the soil environment there exists naturally occurring chitinase producing microorganisms. In the above ground domain, a significant killing effect could be obtained with the basal broth composition alone. The combination of the chitinase broth and basal broth in selected ratios, with a ratio of 1:1 being preferred, produces the desired killing effect for the reasons described above.

Finally, the rapid and prolific root and canopy growth that has been observed may be due to the production of plant growth promoting hormones by soil microorganisms utilizing the substances present in the composition. It is known that the plant growth hormone indole acetic acid is produced by the soil fungi Rhizopus spp. from the amino acid tryptophane. The protein sources used in the basal broth contain this amino acid.

Therefore, the basal broth and chitinase broth composition, method for preparing and using the same of the present invention operate to ensure that pests, and particularly insects, can be controlled to such an extent that they no longer constitute a threat to the human food supply or to present other hazards or adverse consequences to humans, animals or the environment and have been shown to have an absence of components which are known to be toxic or otherwise hazardous to humans or animals, even when coming into direct contact therewith. The above composition operates immediately to eradicate a host of different varieties of pests, and particularly insects and can be employed by using existing distribution means without requiring equipment specifically adapted for the purpose.

COMPOSITIONS USING BASAL BROTH AND CHITINASE BROTH

A composition of mixtures of basal broth and the chitinase broth, prepared as described in Example I above (the "Basal/Chitinase Solution"), were subject to studies to identify class of the active ingredients. The tests were conducted as follows.

Anti-fungal and nematode activity was determined on the two components of the basal broth and chitinase broth and on the Basal/Chitinase Solution using assay techniques well known to persons skilled in its art. It was determined that the most important components of the active ingredients are classified as organic enzymes and a fungal-antimetabolite.

COMPOSITIONS COMPRISING A CHEMICAL FUNGICIDE HAVING SYNERGISM WITH THE BASAL/CHITINASE SOLUTION FOR ENHANCING ANTI-FUNGAL ACTIVITY OF THE CHEMICAL FUNGICIDE

The importance of the enzymes has been demonstrated by preparing a batch of basal broth without adding the enzymes papain or pancreatin. This was then tested for anti-fungal activity. The results were far below the activity of the Basal/Chitinase Solution. This suggests that the enzymes are very important for anti-fungal activity. Along with this evidence, there are several other key pieces that point to the enzymes as having the significant role in the activity of the Basal/Chitinase Solution. First, the size of the clearing zones on skim milk agar plates decreased with the age of the of the Basal/Chitinase Solution, which correlates with the decreasing anti-fungal activity described above. Secondly, autoclaving of the Basal/Chitinase Solution shows a significant loss of anti-fungal activity demonstrating that the anti-fungal agent is at least partially heat unstable or labile. As is known to a person skilled in the art, enzymes are at least partially heat labile.

ANTI-FUNGAL ASSAYS OF THE BASAL/CHITINASE SOLUTION

In order to determine the synergism of anti-fungal activity between the Basal/Chitinase Solution and certain fungicides the following exemplary fungicides were used:

(a) Captan;

(b) Manzate;

(c) Chloroneb; and (d) Myclobutanil.

Inhibition assays were carried out using a Basal/Chitinase Solution as prepared in Example I. PDA plates and assay testing techniques were used that are known to those skilled in the art. The PDA plates were made with dilutions of the Basal/Chitinase Solution of 1:200 and the fungicides were used at 0.5 ug/mL. All plates were run in triplicate and the following fungi were tested for growth inhibition:

FUNGI USED IN INHIBITATION ASSAY TESTS (A) *Pythiumultimum;*

(B) *Thielaviopsis basicola;* and (C) *Rhizoctonia solani.*

The results are shown in Table A below:

TABLE A

INHIBITION OF FUNGAL GROWTH

| Fungus | Plate/Sample | Inhibition (Percent) |
|---|---|---|
| *Pythium ultimum* | PDA | 0 |
| | 0.5 ug/mL Captan | 6 |
| | 1:200 Basal/Chitinase Solution | 13 |
| | Captan + Basal/Chitinase Solution | 58 |
| | PDA | 0 |
| | 0.5 ug/mL Manzate | 8 |
| | 1:200 Basal/Chitinase Solution | 13 |
| | Manzate + Basal/Chitinase Solution | 53 |
| *Thielaviopsis basicola* | PDA | 0 |
| | 0.5 ug/mL Myclobutanil | 14 |
| | 1:200 Basal/Chitinase Solution | 55 |
| | Myclobutanil + Basal/Chitinase Solution | 65 |
| *Rhizoctonia solani* | PDA | 0 |
| | 0.5 ug/mL Manzate | 5 |
| | 1:200 Basal/Chitinase Solution | 16 |
| | Manzate + Basal/Chitinase Solution | 41 |

TABLE A-continued

INHIBITION OF FUNGAL GROWTH

| Fungus | Plate/Sample | Inhibition (Percent) |
| --- | --- | --- |
| | PDA | 0 |
| | 0.5 ug/mL Chloroneb | 2 |
| | 1:200 Basal/Chitinase Solution | 16 |
| | Chloroneb + Basal/Chitinase Solution | 43 |

The results set forth in Table A above shows that a synergism exists between the Basal/Chitinase Solution. The increased anti-fungal activity of *Pythium ultimum*, Captan and Manzate as well as *Rhizoctonia solani*, Manzate and Chloroneb is apparent and shows that selection of a chemical pesticide having synergism with the Basal/Chitinase Solution results in enhanced anti-fungal activity. Synergism occurs when the results of the composition is greater or better than just the results of the additives and the composition.

The synergism of the Basal/Chitinase Solution or basal solution alone with a broad spectrum of chemical fungicides may, to some extent, be dependent on the mode of action such as contact mode or systemic mode. Based on the above inhibition analysis results, similar synergism can be expected on other fungi, such as for example Verticillium and Dahliaie.

However, it is apparent from the above data that similar synergism can be clearly obtained from the contract mode chemical fungicides.

It is noted that a reduced synergism exists for Myclobutanil and *Thielaviopsis basicola* and the reasons therefor cannot be explained from the above data.

In order to support that that the enzymes contained in the Basal/Chitinase Solution are heat labile and can affect the synergism between the Basal/Chitinase Solution and the chemical fungicide, samples of the Basal/Chitinase Solution were autoclaved and the following results obtained are shown on Table B below:

TABLE B

SYNERGISM WITH AUTOCLAVED BASAL/CHITINASE SOLUTION

| Fungus | Plate/Sample | Inhibition (Percent) |
| --- | --- | --- |
| *Pythium ultimum* | PDA | 0 |
| | 0.5 ug/mL Manzate | 4 |
| | 1:200 Basal/Chitinase Solution | 28 |
| | 1:200 Autoclaved Basal/Chitinase Solution | 0 |
| | Manzate + Autoclaved Basal/Chitinase Solution | 4 |

As shown in Table B above, no synergism existed after the Basal/Chitinase Solution alone or with Manzate were autoclaved.

The utility of the above compositions is for the control and suppression of disease and nematodes. Using the teachings of this invention, the following products can be used for treatment of plants, crops and soil:

| Product | Application/Treatment |
| --- | --- |
| Basal/Chitinase Solution/composition | Treatment of plants and soil for disease and nematodes |
| Fungicide solution/composition formed of a Basal/Chitinase Solution and a chemical pesticide, such as for example, Captan, Manzate, Chloroneb or Myclobutanil having synergism with the active ingredients | Treatment of plants, crops and soil for disease and nematodes and fungi responsive to the active ingredients |
| Root Stimulator formed of a Basal/Chitinase Solution/composition and a chemical pesticide, such as for example, Captan, Manzate, Chloroneb or Myclobutanil having synergism with the active ingredients | Treatment of roots of plants, crops and soil for disease and nematodes and fungi responsive to the active ingredients; Use as treatment for seed coating, at planting with seed, seed starting and in furrow application |
| Spray Adjuvant formed of a Basal/Chitinase Solution/composition and a chemical pesticide, such as for example, Captan, Manzate or Chloroneb having synergism with the active ingredients | Treatment of plants, crops and soil for disease and nematodes and fungi responsive to the active ingredients; Use as treatment for seed coating, at planting with seed, seed starting and in furrow application |
| Biological Surfactant formed of a Basal/Chitinase Solution/composition and standard chemical fungicide and insecticides together with a surface-active agent comprising a soluble compound that reduces the surface tension of liquids, or reduces interfacial tension between two liquids or a liquid and a solid; one example of an surface-active agent SYLGARD 309 organic silicone surfactant | Treatment of roots of plants, crops and soil for disease and nematodes and fungi responsive to the active ingredients which can increase the anti-fungi activity such that lower rates of chemical fungicides or pesticides can be used to increase the spectrum of activity |

The use of Basal/Chitinase Solution or a basal solution or basal composition alone may be used with any one of the chemical fungicides listed in the Chemical Fungicide Reference, listed above, and it is anticipated that, based on the mode of action, at least some synergism will occur and some increase in anti-fungal activity is expected.

It is envisioned that the use of the Basal/Chitinase Solution or a basal solution or basal composition alone, which appear to contain the active ingredients, can be likewise be intermixed with standard chemical pesticides and insecticides. Inhibitation Assay Testing using the teaching disclosed herein is one method for identifying those chemical pesticides and insecticides that have synergism with the active ingredients and which can have its anti-fungal activity enhanced using a composition comprising the Basal/Chitinase Solution or the basal solution or basal composition alone.

The examples disclosed herein do not cover all of the possible chemical pesticides, insecticides and fungi that can be expected to exhibit increased anti-fungal activity using the teachings of this invention. The inhibition assay testing is one method for identifying increased anti-fungal activity which is responsive to the active ingredients in the Basal/Chitinase Solution or the basal solution or basal composition alone. There are other methods available to those skilled in the art to make such a determination.

Although the invention has been herein shown and described in what is conceived to be the most practical and preferred embodiments including method of preparing a composition having selected ratios of chitinase broth to basal broth and methods of using the so formed chitinase broth and basal broth as biochemical agents, it is recognized that departures may be made therefrom within the scope of the invention which is not to be limited to the illustrative details disclosed.

What is claimed is:

1. An insecticidal composition comprising effective amounts of a basal broth, a chitinase broth and a chemical fungicide wherein said fungicide has synergism with the basal broth and the chitinase broth.

2. The composition of claim 1 wherein the basal broth comprises pancreatin, papain, sugar, potassium phosphate, hydrolyzed protein, flour having about 50% protein and water at a pH of about 7.5.

3. The composition of claim 1 wherein the chitinase broth comprises chitin, water and a chitinase-producing bacterial culture.

4. The composition of claim 2 wherein the chemical fungicide is a contact mode fungicide.

5. The composition of claim 2 wherein the chemical fungicide is a systemic mode fungicide.

6. The composition of claim 2 wherein the chemical fungicide is a member selected from the group consisting of Captan, Maizate, Chloroneb and Myclobutanil.

7. An insecticidal composition comprising effective amounts of a basal broth, a chitinase broth and a chemical fungicide wherein said fungicide has synergism with the basal broth and the chitinase broth wherein the basal broth comprises pancreatin, papain, sugar, potassium phosphate, hydrolyzed protein, flour having about 50% protein and water at a pH of about 7.5 and wherein the chitinase broth comprises chitin, water and a chitinase-producing bacterial culture.

8. The composition of claim 7 wherein the chemical fungicide is a contact mode fungicide.

9. The composition of claim 7 wherein the chemical fungicide is a systemic mode fungicide.

10. The composition of claim 7 wherein the chemical fungicide is a member selected from the group consisting of Captan, Manzate, Chloroneb and Myclobutanil.

11. A method of preparing an insecticidal composition comprising a basal broth, a chitinase broth and a chemical fungicide wherein said fungicide has synergism with the basal and chitinase broths comprising the steps:
   (A) intermixing water, chitin, a chitinase-producing bacterial culture and a buffer to make a chitinase broth having a ph of about 7;
   (B) intermixing water, protein, pancreatin and papain and a buffer to make a basal broth having a pH of about 7;
   (C) intermixing effective amounts of the chitinase and basal broths to make a basal composition; and
   (D) intermixing an effective amount of the chemical fungicide with the basal composition to make the insecticidal composition.

12. The method of claim 11 wherein the bacterial culture is *Streptomyces griseus*.

13. The method of claim 12 wherein the intermixing step to make the chitinase broth further comprises intermixing dipotassium phosphate, magnesium sulfate, iron sulfate, zinc sulfate, manganese sulfate and phosphoric acid to make the chitinase broth.

14. The method of claim 11 wherein the protein of the basal broth is hydrolyzed for about 2 hr at about 40° C. before intermixing with the chitinase broth.

15. The method of claim 14 further comprising the step of aging the insecticidal composition for 24–48 hr.

16. The method of claim 11 wherein the intermixing step to make the basal broth further comprises intermixing sucrose, sodium chloride and potassium hydroxide to make the basal broth.

17. The method of claims 11 wherein the intermixing step to make the basal composition further comprises intermixing the basal broth and the chitinase broth in an equal ratio by fluid volume to make the basal composition.

18. The method of claim 11 wherein the intermixing step to make the basal composition further comprises intermixing the chitinase broth and the basal broth in a 2:1 ratio, respectively, by fluid volume to make the basal composition.

19. The method of claims 11 wherein the intermixing step to make the basal composition further comprises intermixing the chitinase broth and the basal broth in a 1:2 ratio, respectively, by fluid volume to make the basal composition.

20. A method of preparing an insecticidal composition comprising a basal broth, a chitinase broth and a chemical fungicide wherein said fungicide has synergism with the basal and chitinase broths comprising the steps:
   (A) intermixing water, chitin, a bacterial culture comprising *Streptonlyces grisell*, dipotassium phosphate, magnesium sulfate, iron sulfate, zinc sulfate, manganese sulfate, phosphoric acid and a buffer to make a chitinase broth having a pH of about 7;
   (B) allowing fermentation and production of chitinase to occur in said broth;
   (C) dissolving sweet whey protein in water to make a whey solution;
   (D) adding soybean flour having about 50% protein, pancreatin, papain and potassium hydroxide solution to the whey solution to allow protein hydrolysis to occur resulting in a hydrolyzed protein broth;
   (E) intermixing sucrose and sodium chloride with the hydrolyzed protein broth and heating the resulting mixture to make a basal broth;
   (F) intermixing effective amount of the chitinase and basal broths to make a basal composition; and
   (G) intermixing and effective amount of the chemical fungicide with an effective amount of the basal composition to make the insecticidal composition.

21. The method of claim 20 further comprising the step of aging the insecticidal composition for a period of time.

22. The method of claim 21 wherein the period of time is about 48 hr.

23. The method of claim 20 wherein the temperature of the protein hydrolysis in step (D) occurs at about 40° C.

24. The method of claim 20 wherein the temperature of protein hydrolysis in step (D) occurs in a pH range of about 5 to about 9.

25. The method of claim 20 wherein the step of protein hydrolysis (D) occurs at a temperature of about 90° C. and a pH range of about 5 to about 9.

26. The method of claim 20 wherein the pH of the insecticidal composition is 7.5.

27. The method of claim 20 wherein the intermixing step to make the basal composition of step (F) further comprises intermixing the basal broth and the chitinase broth in an equal ratio by fluid volume to make the basal composition.

28. The method of claim 20 wherein the intermixing step to make the basal composition of step (F) further comprises intermixing the chitinase broth and the basal broth in a 2:1 ratio, respectively, by fluid volume to make the basal composition.

29. The method of claim 20 wherein the intermixing step to make the basal composition of step (F) further comprises intermixing the chitinase broth and the basal broth in a 1:2 ratio, respectively, by fluid volume to make the basal composition.

30. A method of enhancing growth of crops comprising contacting crops with an effective amount of an insecticidal composition comprising a basal broth having hydrolyzed protein, pancreatin, papain, sugar and salt at a pH of 7.5, a chitinase broth and a chemical fungicide.

31. The method of claim 30 wherein the time of contact is about 48 hr.

32. The method of claim 30 wherein the chitinase broth comprises water, chitin and a chitinase-producing bacterial culture.

* * * * *